United States Patent
Yamanishi et al.

(10) Patent No.: US 8,334,136 B2
(45) Date of Patent: Dec. 18, 2012

(54) METHOD FOR PROMOTING HAIR GROWTH OR HAIR REGENERATION BY MAINTAINING OR INCREASING EXPRESSION OF CELL-ADHESION FACTOR

(75) Inventors: Haruyo Yamanishi, Yokohama (JP); Tsutomu Soma, Yokohama (JP); Yuzo Yoshida, Yokohama (JP); Yumiko Ishimatsu, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 97 days.

(21) Appl. No.: 12/842,205

(22) Filed: Jul. 23, 2010

(65) Prior Publication Data

US 2011/0112019 A1 May 12, 2011

Related U.S. Application Data

(60) Provisional application No. 61/213,888, filed on Jul. 24, 2009.

(51) Int. Cl.
*C12N 5/071* (2010.01)
(52) U.S. Cl. ......................................... 435/325; 435/375
(58) Field of Classification Search ................... 435/325
See application file for complete search history.

(56) References Cited

FOREIGN PATENT DOCUMENTS
WO   WO 2006124356 A2 * 11/2006

\* cited by examiner

*Primary Examiner* — Michele K Joike
*Assistant Examiner* — Antonio Galisteo Gonzalez
(74) *Attorney, Agent, or Firm* — Foley & Lardner LLP

(57) ABSTRACT

An object of the present invention is to promote hair growth or hair regeneration by promoting formation and/or regeneration of hair follicles. A method is provided for promoting formation and/or regeneration of hair follicles, comprising maintaining or increasing expression of one or a plurality of genes involved in cell adhesion in dermal papilla cells.

2 Claims, 3 Drawing Sheets

METHOD FOR PROMOTING HAIR GROWTH OR HAIR REGENERATION BY MAINTAINING OR INCREASING EXPRESSION OF CELL-ADHESION FACTOR

SEQUENCE LISTING

The instant application contains a Sequence Listing which has been submitted in ASCII format via EFS-Web and is hereby incorporated by reference in its entirety. Said ASCII copy, created on Oct. 9, 2012, is named sequence.txt and is 144,512 bytes in size.

TECHNICAL FIELD

The present invention relates to a method for promoting hair follicle formation and/or regeneration by maintaining or increasing expression of a gene involved in cell adhesion in dermal papilla cells, a method for screening drugs that promote hair follicle formation and/or regeneration using as an indicator increased expression of a gene involved in cell adhesion in dermal papilla cells, and a method for culturing dermal papilla cells in which expression of a gene involved in cell adhesion has been maintained or increased.

BACKGROUND ART

In reflection of modern society with its growing size of the elderly population and increasing levels of stress, opportunities for exposure to the risk of scalp hair loss due to various factors are continuing to increase, and there is an extremely high demand to compensate for hair loss accompanying aging and the like. Aesthetic or medical efforts are being made to accommodate this situation, including not only the use of hair tonic and hair restoration products, but also actual hair growth and hair transplants. Moreover, accompanying technical breakthroughs attributable to recent progress in stem cell research as well as in consideration of a serious shortage of donors due to problems with tissue compatibility along with ethical demands with respect to criteria for determination of brain death, extremely high, and perhaps somewhat excessive, expectations are being placed on regenerative medical technology as a form of advanced medicine to take the place of conventional organ transplants, resulting in a level of attention higher than ever before being placed on hair follicle regeneration as a model organ of regenerative medicine.

The mechanism of hair follicle formation in the developmental stage has research comparatively extensively, and hair follicles have been determined to be formed as a result of complex interactions between epithelial cells (epidermal cells) and mesenchymal cells lying directly there below (hair papilla cells or dermal papilla cells (DPC)) mediated by signal transduction (R. Pause, et al., N. Engl. J. Med., 341, 491-497, 1999 (Non-Patent Document 1); K. S. Stenn, et al., Physiol. Rev., 81, 449-494, 2001 (Non-Patent Document 2); S. E. Miller, et al., J. Invest. Dermatol., 118, 216-225, 2002 (Non-Patent Document 3). In addition, once formed, hair follicles are organs that undergo repeated cyclical regeneration consisting of a growth phase, transition phase and resting phase, and although numerous physiologically active substances, such as growth factors, cytokines, hormones or neuropeptides, are known to be involved in their regulation, these physiologically active substances do not necessarily coincide with those involved in the mechanism of hair follicle formation in the developmental stage.

It has been determined from mouse hair follicle reconstruction experiments using nude mice that both epithelial cells and mesenchymal cells are essential for hair follicle regeneration, and that hair follicle regeneration is not induced unless at least a fixed number of cells are present (Kishimoto, J., et al., Proc. Natl. Acad. Sci., 96, 7336-7341, 1999 (Non-Patent Document 4). Moreover, although it also been demonstrated that chimeric hair follicles composed of mouse DPC and human epithelial cells can be regenerated (Japanese Unexamined Patent Publication No. 2005-132813 (Patent Document 1); Ehama, et al., 26th Annual Conference of the Molecular Biology Society of Japan, Collection of Lecture Abstracts 2PC-024, 2003 (Non-Patent Document 5)), complete regeneration of human hair follicles has yet to be achieved. One reason for this is that it is difficult to obtain an amount of human DPC capable of inducing hair follicles that is adequate for use in transplantation.

Although cells such as DP that express versican, for example, under specific conditions have been shown to have the ability to specifically induce hair follicles (Kishimoto, J., et al., Proc. Natl. Acad. Sci., 96, 7336-7341, 1999 (Non-Patent Document 4)), the mechanism regarding induction of hair follicle formation at the molecular level remains largely unknown.

Although numerous factors are thought to be involved and function in hair growth of the hair cycle and the mechanism of hair restoration in this manner, there are also thought to be numerous proteins and expression genes thereof for which involvement is still not known, and considerable expectations are currently being placed on elucidation of the details thereof. Elucidation of the mechanisms of hair growth and hair restoration will be extremely useful in the development of methods for promoting hair follicle formation and/or regeneration and the development of drugs used for that purpose, as well as in terms of further advancement of regenerative medical technology and the like.

PRIOR ART DOCUMENTS

Patent Documents

[Patent Document 1] Japanese Unexamined Patent Publication No. 2005-132813

Non-Patent Documents

[Non-Patent Document 1] R. Pause, et al., N. Engl. J. Med., 341, 491-497, 1999
[Non-Patent Document 2] K. S. Stenn, et al., Physiol. Rev., 81, 449-494, 2001
[Non-Patent Document 3] S. E. Miller, et al., J. Invest. Dermatol., 118, 216-225, 2002
[Non-Patent Document 4] Kishimoto, J., et al., Proc. Natl. Acad. Sci., 96, 7336-7341, 1999
[Non-Patent Document 5] Ehama, et al., 26th Annual Conference of the Molecular Biology Society of Japan, Collection of Lecture Abstracts 2PC-024, 2003

SUMMARY OF THE INVENTION

Problems to be Solved by the Invention

An object of the present invention is to promote hair growth or hair regeneration by promoting hair follicle formation and/or regeneration.

Means for Solving the Problems

As a result of conducting microarray analyses of gene expression in dermal papilla cells (DP), dermal sheath cells (DS) and fibroblasts (FB), the inventors of the present invention surprisingly found that genes involved in cell adhesion, for which expression had heretofore not been known in dermal papilla cells, are expressed at high frequency in these dermal papilla cells. Moreover, since expression levels of these genes involved in cell adhesion increase considerably when basic fibroblast growth factor (bFGF), which is known to have an action that maintains the ability to induce hair follicles, contacts dermal papilla cells (DP), these genes involved in cell adhesion are presumed to be intimately involved in the hair follicle formation and/or regeneration function of dermal papilla cells.

Thus, the present application includes the following inventions:

[1] a method for promoting formation and/or regeneration of hair follicles, comprising: maintaining or increasing expression of one or a plurality of genes (belonging to GO:7155) involved in cell adhesion in dermal papilla cells;

[2] the method described in [1], wherein the gene involved in cell adhesion is selected from the group consisting of HAPLN1 (GeneBank registration no.: NM_001884 (SEQ ID NO: 13)), COL8A2 (GeneBank registration no.: NM_005202 SEQ ID NO: 14)), NRCAM (GeneBank registration no.: NM_005010 (SEQ ID NO: 15)), JAM2 (GeneBank registration no.: NM_021219 (SEQ ID NO: 16)), EDIL3 (GeneBank registration no.: NM_005711 (SEQ ID NO: 17)), CX3CL1 (GeneBank registration no.: NM_002996 (SEQ ID NO: 18)), CDON (GeneBank registration no.: NM_016952 (SEQ ID NO: 19)), HMCN1 (GeneBank registration no.: NM_031935 (SEQ ID NO: 20)), LAMC3 (GeneBank registration no.: NM_006059 (SEQ ID NO: 21)), FRAS1 (GeneBank registration no.: NM_025074 (SEQ ID NO: 22)), CDH4 (GeneBank registration no.: AK025855 (SEQ ID NO: 23)), MYBPH (GeneBank registration no.: NM_004997 (SEQ ID NO: 24)), CDHR3 (GeneBank registration no.: NM_152750 (SEQ ID NO: 25)), NRP2 (GeneBank registration no.: NM_201266 (SEQ ID NO: 26)), SLIT2 (GeneBank registration no.: NM_004707 (SEQ ID NO: 27)), FN1 (GeneBank registration no.: NM_212482 (SEQ ID NO: 28)), PVRL3 (GeneBank registration no.: BC017572 (SEQ ID NO: 29)), ITGBL1 (GeneBank registration no.: NM_004791 (SEQ ID NO: 30)), PVRL3 (GeneBank registration no.: NM_015480 (SEQ ID NO: 31)), PVRL3 (GeneBank registration no.: BC017572) and NRP2 (GeneBank registration no.: NM_201266);

[3] the method described in [2], wherein the gene involved in cell adhesion is selected from the group consisting of COL8A2 (GeneBank registration no.: NM_005202), NRCAM (GeneBank registration no.: NM_005010), JAM2 (GeneBank registration no.: NM_021219), LAMC3 (GeneBank registration no.: NM_006059), HMCN1 (GeneBank registration no.: NM_031935) and CDON (GeneBank registration no.: NM_016952);

[4] the method described in [3], wherein the gene involved in cell adhesion is JAM2 (GeneBank registration no.: NM_021219) or LAMC3 (GeneBank registration no.: NM_006059);

[5] a method for screening drugs that promote hair follicle formation and/or regeneration, comprising: contacting a candidate drug with dermal papilla cells, and evaluating the candidate drug to be a drug that promotes formation and/or regeneration of hair follicles in the case expression of one or a plurality of genes involved in cell adhesion (belonging to GO:7155) in the dermal papilla cells increases;

[6] the screening method described in [5], wherein the gene involved in cell adhesion is selected from the group consisting of HAPLN1 (GeneBank registration no.: NM_001884), COL8A2 (GeneBank registration no.: NM_005202), NRCAM (GeneBank registration no.: NM_005010), JAM2 (GeneBank registration no.: NM_021219), EDIL3 (GeneBank registration no.: NM_005711), CX3CL1 (GeneBank registration no.: NM_002996), CDON (GeneBank registration no.: NM_016952), HMCN1 (GeneBank registration no.: NM_031935), LAMC3 (GeneBank registration no.: NM_006059), FRAS1 (GeneBank registration no.: NM_025074), CDH4 (GeneBank registration no.: AK025855), MYBPH (GeneBank registration no.: NM_004997), unknown gene symbol (GeneBank registration no.: NM_152750), NRP2 (GeneBank registration no.: NM_201266), SLIT2 (GeneBank registration no.: NM_004787), FN1 (GeneBank registration no.: NM_212482), PVRL3 (GeneBank registration no.: BC017572), ITGBL1 (GeneBank registration no.: NM_004791), PVRL3 (GeneBank registration no.: NM_015480), PVRL3 (GeneBank registration no.: BC017572) and NRP2 (GeneBank registration no.: NM_201266);

[7] the screening method described in [6], wherein the gene involved in cell adhesion is selected from the group consisting of COL8A2 (GeneBank registration no.: NM_005202), NRCAM (GeneBank registration no.: NM_005010), JAM2 (GeneBank registration no.: NM_021219), LAMC3 (GeneBank registration no.: NM_006059), HMCN1 (GeneBank registration no.: NM_031935) and CDON (GeneBank registration no.: NM_016952);

[8] the screening method described in [7], wherein the gene involved in cell adhesion is JAM2 (GeneBank registration no.: NM_021219) or LAMC3 (GeneBank registration no.: NM_006059);

[9] a method for culturing dermal papilla cells that maintain the ability to induce hair follicles, comprising: maintaining or increasing expression of one or a plurality of genes involved in cell adhesion (belonging to GO:7155) in the dermal papilla cells, and sub culturing those dermal papilla cells in which expression of the gene involved in cell adhesion has been maintained or increased;

[10] the method for culturing dermal papilla cells described in [9], wherein the gene involved in cell adhesion is selected from the group consisting of HAPLN1 (GeneBank registration no.: NM_001884), COL8A2 (GeneBank registration no.: NM_005202), NRCAM (GeneBank registration no.: NM_005010), JAM2 (GeneBank registration no.: NM_021219), EDIL3 (GeneBank registration no.: NM_005711), CX3CL1 (GeneBank registration no.: NM_002996), CDON (GeneBank registration no.: NM_016952), HMCN1 (GeneBank registration no.: NM_031935), LAMC3 (GeneBank registration no.: NM_006059), FRAS1 (GeneBank registration no.: NM_025074), CDH4 (GeneBank registration no.: AK025855), MYBPH (GeneBank registration no.: NM_004997), unknown gene symbol (GeneBank registration no.: NM_152750), NRP2 (GeneBank registration no.: NM_201266), SLIT2 (GeneBank registration no.: NM_004787), FN1 (GeneBank registration no.: NM_212482), PVRL3 (GeneBank registration no.: BC017572), ITGBL1 (GeneBank registration no.: NM_004791), PVRL3 (GeneBank registration no.: NM_015480), PVRL3 (GeneBank registration no.: BC017572) and NRP2 (GeneBank registration no.: NM_201266);

[11] the method for culturing dermal papilla cells described in [10], wherein the gene involved in cell adhesion is selected from the group consisting of COL8A2 (GeneBank registration no.: NM_005202), NRCAM (GeneBank registration no.: NM_005010), JAM2 (GeneBank registration no.: NM_021219), LAMC3 (GeneBank registration no.: NM_006059), HMCN1 (GeneBank registration no.: NM_031935) and CDON (GeneBank registration no.: NM_016952);

[12] the method for culturing dermal papilla cells described in [11], wherein the gene involved in cell adhesion is JAM2 (GeneBank registration no.: NM_021219) or LAMC3 (GeneBank registration no.: NM_006059);

[13] an aesthetic method for promoting hair follicle formation and/or regeneration, comprising: maintaining or increasing expression of one or a plurality of genes involved in cell adhesion (belonging to GO:7155) in dermal papilla cells; and,

[14] a therapeutic method for promoting hair follicle formation and/or regeneration, comprising: maintaining or increasing expression of one or a plurality of genes involved in cell adhesion (belonging to GO:7155) in dermal papilla cells.

Effects of the Invention

According to the present invention, the formation and/or regeneration of hair follicles can be promoted, and as a result thereof, hair growth or hair regeneration can be promoted.

EMBODIMENTS OF THE INVENTION

Figure 1:
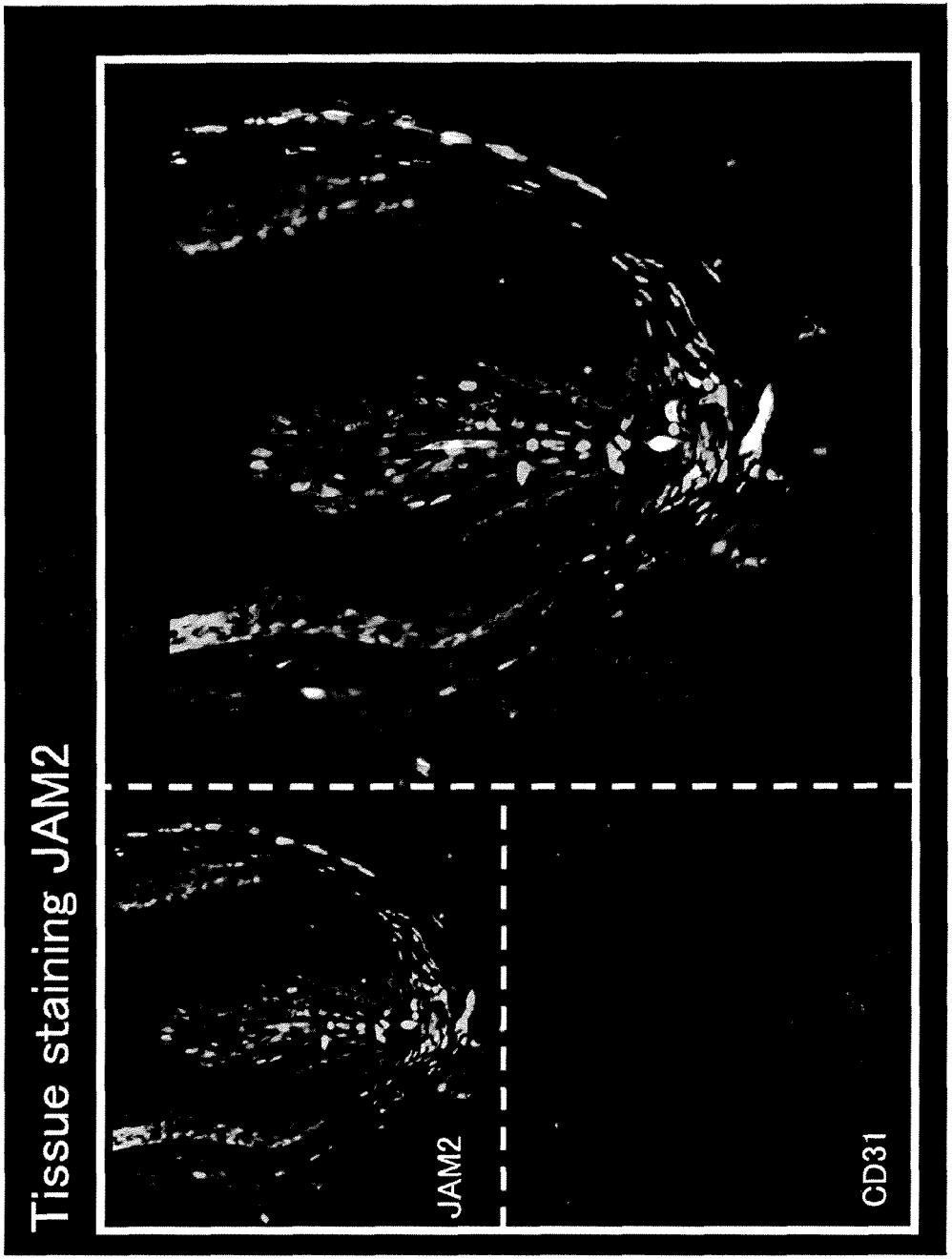
FIG. 1 is a photograph showing tissue staining of JAM2 in dermal papilla cells.

In a first aspect thereof, the present invention provides a method for promoting hair follicle formation and/or regeneration by maintaining or increasing expression of one or a plurality of genes involved in cell adhesion in dermal papilla cells.

Dermal papilla cells refer to mesenchymal cells that mainly compose dermal papilla located within the hair bulbus inside hair follicles, and fulfill the role of a control tower in terms of transmitting signals that activate follicular epithelial cells for self-regeneration of hair follicles (Japanese Unexamined Patent Publication No. 2005-110540). Thus, hair growth or hair regeneration can be promoted by promoting formation and/or regeneration of hair follicles by activating this function of dermal papilla cells.

A gene involved in cell adhesion refers to a gene that encodes proteins involved in adhesion between cells in multicellular organisms (cell adhesion factor), and plays an important role in cell adhesion factors present in the extracellular matrix and membrane and in the cytoskeleton as an intracellular connecting substance of cell adhesion factors. In the case of using in the description of the present application, a gene involved in cell adhesion specifically refers to all genes categorized in cell adhesion category GO:7155 in the field of gene ontology. Gene ontology refers to a concept for classifying and organizing genes that has developed accompanying the importance of techniques for visually representing gene expression profiling, clustering, annotation and the vast amount of data thereof during the recent development of comprehensive analytical technologies such as microarrays, and information relating to various genes has been compiled in a database. In gene ontology, genes are classified and organized according to molecular function, biological process and cellular components, and inter-attribute inheritance relationships are defined for each classification method. Definition of attributes and inter-attribute inheritance relationships are available from the Gene Ontology Consortium (www.geneontology.org). The cell adhesion category GO:7155 is a sub-category of biological process, and more specifically, 1053 genes belong to this category.

Preferable examples of the aforementioned genes involved in cell adhesion include HAPLN1 (GeneBank registration no.: NM_001884), COL8A2 (GeneBank registration no.: NM_005202), NRCAM (GeneBank registration no.: NM_005010), JAM2 (GeneBank registration no.: NM_021219), EDIL3 (GeneBank registration no.: NM_005711), CX3CL1 (GeneBank registration no.: NM_002996), CDON (GeneBank registration no.: NM_016952), HMCN1 (GeneBank registration no.: NM_031935), LAMC3 (GeneBank registration no.: NM_006059), FRAS1 (GeneBank registration no.: NM_025074), CDH4 (GeneBank registration no.: AK025855), MYBPH (GeneBank registration no.: NM_004997), unknown gene symbol (GeneBank registration no.: NM_152750), NRP2 (GeneBank registration no.: NM_201266), SLIT2 (GeneBank registration no.: NM_004787), FN1 (GeneBank registration no.: NM_212482), PVRL3 (GeneBank registration no.: BC017572), ITGBL1 (GeneBank registration no.: NM_004791), PVRL3 (GeneBank registration no.: NM_015480), PVRL3 (GeneBank registration no.: BC017572) and NRP2 (GeneBank registration no.: NM_201266). More preferably, the gene involved in cell adhesion is COL8A2 (GeneBank registration no.: NM_005202), NRCAM (GeneBank registration no.: NM_005010), JAM2 (GeneBank registration no.: NM_021219), LAMC3 (GeneBank registration no.: NM_006059), HMCN1 (GeneBank registration no.: NM_031935) or CDON (GeneBank registration no.: NM_016952), while most preferably, the gene involved in cell adhesion is JAM2 (GeneBank registration no.: NM_021219) or LAMC3 (GeneBank registration no.: NM_006059).

Although these genes involved in cell adhesion are expressed in vascular endothelial cells, skin basement membrane and the like, and are thought to play an important role in cell adhesion factors present in the extracellular matrix and membrane and in the cytoskeleton as intracellular connecting substances of cell adhesion factors, the fact that these genes are highly expressed in dermal papilla cells was extremely unexpected. In addition, the inventors of the present invention also observed in immunostaining tests that JAM2 and LAMC3 are actually expressed in dermal papilla cells as genes involved in cell adhesion. JAM2 is a gene that encodes junctional adhesion molecule 2, and this junctional adhesion molecule is continuously formed in a sealed state around epithelial and endothelial cells, and functions as a physical barrier for preventing solutes and water from freely passing through paracellular space. Although JAM2 has been reported to be expressed in the vicinity of blood vessels of mouse skin (ear auricle) (Ludwig, R. J., et al., J. Invest. Dermatol., 125, 969-976, 2005) and in vascular endothelial cells, and be involved in leukocyte infiltration during inflammation (Claire, Q. F., et al., J. Cell. Biol., 178, 549-556, 2007), expression in dermal papilla cells has heretofore been unknown. In addition, LAMC3 has been determined to be a gene that encodes the γ3 chain of laminin, which is an important non-collagen component that composes the basement membrane. This laminin γ3 chain is a constituent of laminin 12, and has been determined to be a prominent element in the apical surfaces of cilia (epithelial cells) of the skin, retina, lungs, fallopian tubes, epididymis, vas deferens and seminiferous tubules. The distribution of apical laminin containing γ3 chains on the surface of cilia epithelium is thought to be important for the morphology and structural stability of the ciliary projections of these cells. Although LAMC3 has been reported to be expressed in human skin basement membrane (Koch, M., et al., J. Cell. Biol., 1999, May 3, 145(30), 605-18) and in the basement membrane of mouse fetuses (Gersdorff, N., et al., J. Biol. Chem., 2005, Jun. 10, 280(23), 22146-53), its expression in dermal papilla cells has heretofore been unknown.

On the basis of the findings of the prior art as described above, since it is extremely unexpected that genes involved in cell adhesion are highly expressed in dermal papilla cells governing function during hair follicle formation and/or regeneration, it is sufficient to presume that genes involved in cell adhesion are involved in the formation and/or regeneration of hair follicles.

Increasing expression of the aforementioned genes in dermal papilla cells can be achieved by, for example, contacting dermal papilla cells with a drug that maintains or increases expression of genes involved in cell adhesion in dermal papilla cells or by using common genetic engineering techniques in the art. For example, when the aforementioned genes are deleted or missing in dermal papilla cells, there are cases in which their expression can be increased by introducing the gene itself into the dermal papilla cells. In addition, although the aforementioned genes are present in dermal papilla cells, when the genes are deficient due to being in an inactive or silent state, expression of those genes can be increased by arranging a regulatory sequence such as a promoter or enhancer that maintains or increases expression of those genes at a location where it can be used by those genes.

The method used to introduce the aforementioned genes, promoter or enhancer into cells may be a gene insertion method using a viral vector, or non-viral gene insertion method (Nikkei Science, April 1994, 20-45, Experimental Medicine Special Edition, 12(15) (1994); Experimental Medicine Supplement, "Basic Technology of Gene Therapy", Yodosha Co., Ltd. (1996)). Examples of gene insertion methods that use a viral vector include methods in which the gene is inserted by incorporating in a DNA virus such as retrovirus, adenovirus, adeno-associated virus, herpes virus, vaccinia virus, pox virus, polio virus or sindbis virus, or an RNA virus. Among these, methods using a retrovirus, adenovirus, adeno-associated virus or vaccinia virus are particularly preferable. Examples of non-viral gene insertion methods include methods in which an expression plasmid is administered directly (DNA vaccine method), liposome methods, lipofectin methods, microinjection, calcium phosphate methods and electroporation, with DNA vaccine and liposome method being particular preferable. In addition, methods used to allow the genes to actually act as pharmaceuticals consist of in vivo methods, in which DNA is introduced directly into dermal papilla cells, and ex vivo methods, in which DNA is introduced into the cells outside the body after which the cells are returned to the body (Nikkei Science, April 1994, 20-45; Pharmaceuticals Monthly, 36(1), 23-48 (1994), Experimental Medicine Special Edition, 12(15) (1994)). In vivo methods are preferable. In the case of administered by an in vivo method, the DNA is administered directly to a site where it is to act, such as a location where hair growth is desired to be promoted. Administration may be subcutaneous or intradermal administration. In the case of administering by an in vivo method, administration is commonly carried out with an injection preparation and the like, and a commonly used vehicle may be added as necessary. In addition, in the case of putting into the form of liposomes or fusogenic liposomes (such as Sendai virus (HJV)-liposomes), DNA can be administered in the form of a liposome preparation such as a suspension, frozen preparation or centrifugally concentrated frozen preparation.

Expression of the aforementioned genes in dermal papilla cells can be determined by, for example, extracting mRNA from the dermal papilla cells and measuring the amount thereof. Extraction and measurement of mRNA are commonly known in the art, and quantification of mRNA is carried out by, for example, a quantitative polymerase chain reaction (PCR). In addition, expression of the aforementioned genes can be determined by directly measuring the amount of expression products of the genes in the dermal papilla cells. For example, this measurement can be carried out by using a specific antibody to the gene expression product and using a commonly known method in the art such as an immunostaining method using a fluorescent substance, pigment or enzyme, Western blotting, an immunoassay method such as ELISA or RIA or various other methods. In addition, in addition to that described above, the expressed amount of the aforementioned genes can be measured by measuring a known biological activity of an expression product of the genes. In addition, expression of the aforementioned genes can also be determined by in situ hybridization or by measuring the biological activity thereof.

In addition, another embodiment of the present invention provides a method for screening drugs that promote hair follicle formation and/or regeneration, comprising: contacting a candidate drug with dermal papilla cells, and evaluating the candidate drug to be a drug that promotes formation and/or regeneration of hair follicles in the case expression of one or a plurality of genes involved in cell adhesion in the dermal papilla cells increases. In this method, a drug that maintains or increases intrinsic expression of a gene involved in cell adhesion in dermal papilla cells is selected as a drug that promotes formation and/or regeneration of hair follicles. Expression of a gene involved in cell adhesion can be determined by extracting mRNA from dermal papilla cells and measuring the amount of gene involved in cell adhesion. Extraction of RNA and measurement of the amount thereof are commonly known in the art, and for example, quantification of mRNA is carried out by a quantitative polymerase chain reaction (PCR). Whether or not expression of the gene has increased can be evaluated by comparing expression levels of the gene relating to cell adhesion before and after the candidate drug has contacted the dermal papilla cells. For example, a candidate drug may be judged to be a drug that promotes hair follicle formation and/or regeneration if intrinsic expression of a gene involved in cell adhesion in epidermal cells has increased, in comparison with a control value, by 30% or more, preferably by 50% or more, more preferably by 70% or more, and most preferably by 100% or more. Although there are no limitations on the control value, it may be, for example, an average value of the intrinsic expression level of the gene involved in cell adhesion in dermal papilla cells at a corresponding site in a statistically significant number (for example, 10 or more and preferably 100 or more) healthy individuals.

In a preferable aspect thereof, the aforementioned screening method includes confirmation of hair growth or hair regeneration effects by applying a candidate drug having the aforementioned increasing ability to a model animal, such as a shaved animal or an animal deficient in the gene involved in cell adhesion.

Still another embodiment of the present invention provides a method for culturing dermal papilla cells that maintain the ability to induce hair follicles, comprising: maintaining or increasing expression of one or a plurality of genes involved in cell adhesion in the dermal papilla cells, and sub-culturing those dermal papilla cells in which expression of the gene involved in cell adhesion has been maintained or increased. In this method, dermal papilla cells are cultured under conditions that enable expression of the aforementioned gene involved in cell adhesion that is intimately related to hair follicle formation to be maintained or increased, and since the ability to regenerate and/or form hair follicles is increased in dermal papilla cells cultured in this manner, these cells can be effectively used for hair follicle and/or hair regeneration and hair transplant through cell transplantation. Although it has been difficult in the prior art to acquire an adequately large number of human dermal papilla cells having the ability to induce hair follicles to enable the cells to be used for transplant, if dermal papilla cells are cultured in accordance with the present invention, an amount of dermal papilla cells having the ability to induce hair follicles that is adequate for transplantation can be prepared even from a small number of dermal papilla cells. As was previously described, increasing expression of the aforementioned genes involved in cell adhesion that are intimately related to hair follicle formation is carried out by, for example, culturing in the presence of a drug that maintains or increases expression of those genes, or by culturing dermal papilla cells in which expression of a gene involved in cell adhesion has been increased by transforming using genetic engineering techniques as previously described. Preferable examples of the aforementioned genes involved in cell adhesion include HAPLN1 (GeneBank registration no.: NM_001884), COL8A2 (GeneBank registration no.: NM_005202), NRCAM (GeneBank registration no.: NM_005010), JAM2 (GeneBank registration no.: NM_021219), EDIL3 (GeneBank registration no.: NM_005711), CX3CL1 (GeneBank registration no.: NM_002996), CDON (GeneBank registration no.: NM_016952), HMCN1 (GeneBank registration no.: NM_031935), LAMC3 (GeneBank registration no.: NM_006059), FRAS1 (GeneBank registration no.: NM_025074), CDH4 (GeneBank registration no.: AK025855), MYBPH (GeneBank registration no.: NM_004997), unknown gene symbol (GeneBank registration no.: NM_152750), NRP2 (GeneBank registration no.: NM_201266), SLIT2 (GeneBank registration no.: NM_004787), FN1 (GeneBank registration no.: NM_212482), PVRL3 (GeneBank registration no.: BC017572), ITGBL1 (GeneBank registration no.: NM_004791), PVRL3 (GeneBank registration no.: NM_015480), PVRL3 (GeneBank registration no.: BC017572) and NRP2 (GeneBank registration no.: NM_201266). More preferably, examples of genes involved in cell adhesion include COL8A2 (GeneBank registration no.: NM_005202), NRCAM (GeneBank registration no.: NM_005010), JAM2 (GeneBank registration no.: NM_021219), LAMC3 (GeneBank registration no.: NM_006059), HMCN1 (GeneBank registration no.: NM_031.935) and CDON (GeneBank registration no.: NM_016952). Culturing is carried out in a suitable medium, such as Dulbecco's modified Eagle's medium containing fetal bovine serum (available from BRL) or Chang's medium (available from Irvine Scientific), preferably in a $CO_2$ atmosphere at a temperature of room temperature to about 37°, and preferably about 37° C., for 1 to 7 days. Cell growth factor, hormones or other trace nutrients can be further added to the medium as necessary. Specific examples thereof include transferrin, insulin, triiodothyronine, glucagon, hydrocortisone, testosterone, estradiol, progesterone and selenium.

Dermal papilla cells that maintain the ability to induce hair follicles obtained according to the culturing method of the present invention described above can be used for research and development on hair follicle transplant and hair follicle reconstruction for the purpose of regenerating hair follicles, as well as for treatment of alopecia and the like.

The following provides a more detailed explanation of the present invention using specific examples thereof. Furthermore, the present invention is not limited by these examples.

EXAMPLES

Culturing of DP, DS and FB

Human dermal papilla cells (DP) were prepared from scalp tissue provided by donors. After removing the dermal tissue, hair follicle sites present in fatty tissue were harvested with tweezers under a stereo microscope and using ophthalmic scissors. The harvested hair follicles were transferred to a culture broth containing antibiotic, and the dermal papilla cell sites were isolated and harvested macroscopically under the same type of microscope. The isolated dermal papilla were cultured for one week or more at 37° C. and 95% $CO_2$ in medium contained in a 10 cm round dish (TRP) and subsequently used in the experiments. The medium used consisted of Advance d-DMEM (Invitrogen), 15% fetal bovine serum, 2 mM L-glutamine and a mixture of penicillin, streptomycin and amphotericin (dilution factor: 100). The cells were suitably sub-cultured under the same conditions. At the time of sub-culturing, the cells were dissociated with 0.25% trypsin/EDTA solution and transferred to a fresh dish followed by sub-culturing in fresh medium of the same composition.

Human dermal sheath cells (DS) were similarly prepared from scalp tissue provided by donors. After removing the dermal tissue, hair follicle sites present in fatty tissue were harvested with tweezers under a stereo microscope and using ophthalmic scissors. The harvested hair follicles were transferred to a culture broth containing antibiotic, and connective tissue root sites were isolated and harvested macroscopically under the same type of microscope. The isolated connective tissue roots were treated with 0.35% collagenase (Wako Pure Chemical Industries) for 40 minutes at 37° C. followed by culturing for one week or more at 37° C. and 95% $CO_2$ in medium contained in a 35 mm collagen-coated dish (AGC Technoglass) and subsequently used in the experiments. The medium used was the same as that described above. The cells were suitably sub-cultured under the same conditions. At the time of sub-culturing, the cells were dissociated with 0.25% trypsin/EDTA solution and transferred to a fresh dish followed by sub-culturing in fresh medium of the same composition.

Commercially available cells (Toyobo) were used for the fibroblasts (FB). The medium used as the same as that described above.

Comparison of Gene Expression Profiles Using a Microarray Method

Total RNA, including mRNA, was recovered from the human dermal papilla cells, human dermal sheath cells and fibroblasts described above using an RNeasy Micro Kit (Qiagen). The recovered RNA was used to synthesize double-stranded cDNA in accordance with the protocol of Agilent, and was followed by synthesis of cRNA labeled with cyanine 3 and cyanine 5. The labeled cRNA was hybridized for 17 hours at 65° C. to a microarray chip slide (Agilent, whole human genome (4×44K), G4110) using a two-color method. Two types each of RNA from the dermal sheath cells of two donors (total of four types), two types each of RNA from dermal papilla cells of two donors, and two types each of RNA from fibroblasts from a single donor were used to respectively compare gene expression levels between DS and DP cells, DP cells and FB and FB and DS cells on each chip slide. After washing the slides, a fluorescent signal (cyanine 3 or cyanine 5) of the cRNA on each slide was imaged with a dual-laser microarray scanner (Agilent). The imaged data was quantified using Feature Extraction Software 9.1, and analysis (tagging) was carried out by marking abnormal values and low values equivalent to background. Comparison of each expression level was carried out by comparing quantified values of the acquired signals between two cells.

The analytical microarray data was analyzed using GeneSpring 7.0. Genes expressed at a level 1.5 times or more higher in DP cells than in DS cells, and genes expressed at a level 1.5 times or more higher in DP cells than in FB were extracted. As a result, 223 genes were extracted. These 223 genes were classified according to gene ontology using GeneSpring followed by subjecting to Fisher's test.

Localization Analysis

Human scalp sections were prepared from scalp tissue provided by donors. The sections were embedded in OTC Compound (Sakura Finetek) and frozen. Frozen sections were prepared with a cryostat and then used for the immunostaining described below. After returning the frozen sections to room temperature and fixing with acetone, the sections were washed with PBS, blocked with DAKO Cytomation Protein Block Serum-Free (DAKO), and antibodies were diluted with 3% BSA-TBST solution. Anti-JAM2 and anti-LAMC3 (Santa Cruz) were respectively used for the antibodies. CD31 (BD Pharmingen) was used for counter-staining. Alexa anti-goat 488, Alexa anti-rabbit 488 and Alexa anti-mouse 594 were used for the secondary antibodies.

Effects of Basic Fibroblast Growth Factor (bFGF)

bFGF is known to maintain the ability to induce hair follicles, which is one of the characteristics of dermal papilla (Osada, A. et al., Tissue Eng., 13, 975, 2007). Therefore, changes in the expression of specific genes in dermal papilla were investigated in the case of culturing cultured DP cells in the presence of bFGF. DP cells were inoculated into a 6-well culture plate, and the medium was replaced with the same medium as that used above containing bFGF (R&D System) or PBS serving as a solvent control. The cells were recovered when they reached confluency followed by use in the RT-PCR analysis described below.

RT-PCR Analysis

RNA was extracted from the cultured DP cells using an RNeasy Kit (Qiagen). An equivalent of 1 µg of each RNA was reverse-transcribed to cDNA in a reaction system consisting of 20 µl of SuperScript II (Invitrogen). 1 µl of the resulting samples was applied to quantitative PCR (LightCycler System, Roche) in a 20 µl system using the primer pairs indicated in Table 1. The reaction protocol of LightCycler FastStart DNA Master SYBR Green I (Roche) (40 cycles consisting of 10 seconds at 95° C., 10 seconds at 30° C. and 15 seconds at 72° C.) was used.

TABLE 1

| | | |
|---|---|---|
| hCOL8A2-F1 | TGTACAAGAACAACGTGCCG | (SEQ ID NO: 1) |
| hCOL8A2-R1 | CGCCTCTGTTCAGCTTTTGT | (SEQ ID NO: 2) |
| hNRCAM-F1 | TGATGCAGAAGACCACAAGC | (SEQ ID NO: 3) |
| hNRCAM-R1 | AGGGCTGACAAACAAGTGCT | (SEQ ID NO: 4) |
| hHMCN1-F1 | GCCTTGAGGGATGAAAACCT | (SEQ ID NO: 5) |
| hHMCN1-R1 | CCAAGGAAGGCACACAAAAC | (SEQ ID NO: 6) |
| hCDON-F3 | AGAGCGTCAAGGACAATGTG | (SEQ ID NO: 7) |
| hCDON-R3 | GTTACCGGCTTGAAGTTGGA | (SEQ ID NO: 8) |
| hJAM2_308-FR | AAAGAAGGGAATCCAGCTCC | (SEQ ID NO: 9) |
| hJAM2 308-R4 | TAGCATACACCAAGGCCACA | (SEQ ID NO: 10) |
| hLAMC3 288-F2 | TACGCGCTTCTCTGGAATCT | (SEQ ID NO: 11) |
| hLAMC3 288-R2 | CTGCCATGATGCAACTGTCT | (SEQ ID NO: 12) |

Results

Analysis of Microarray Data

When the extracted 223 genes were categorized according to gene ontology using GeneSpring and then tested using Fisher's test, 145 of the genes were determined to belong to GO:9987 (cellular process) at a significant difference of $p<0.01$, of which 21 genes were determined to belong to GO:7155 (cell adhesion), and 10 genes were determined to belong to its sub-category of GO:16336 (cell-cell adhesion).

Expression of Gene Involved in Cell Adhesion in Dermal Papilla

Figure 2:
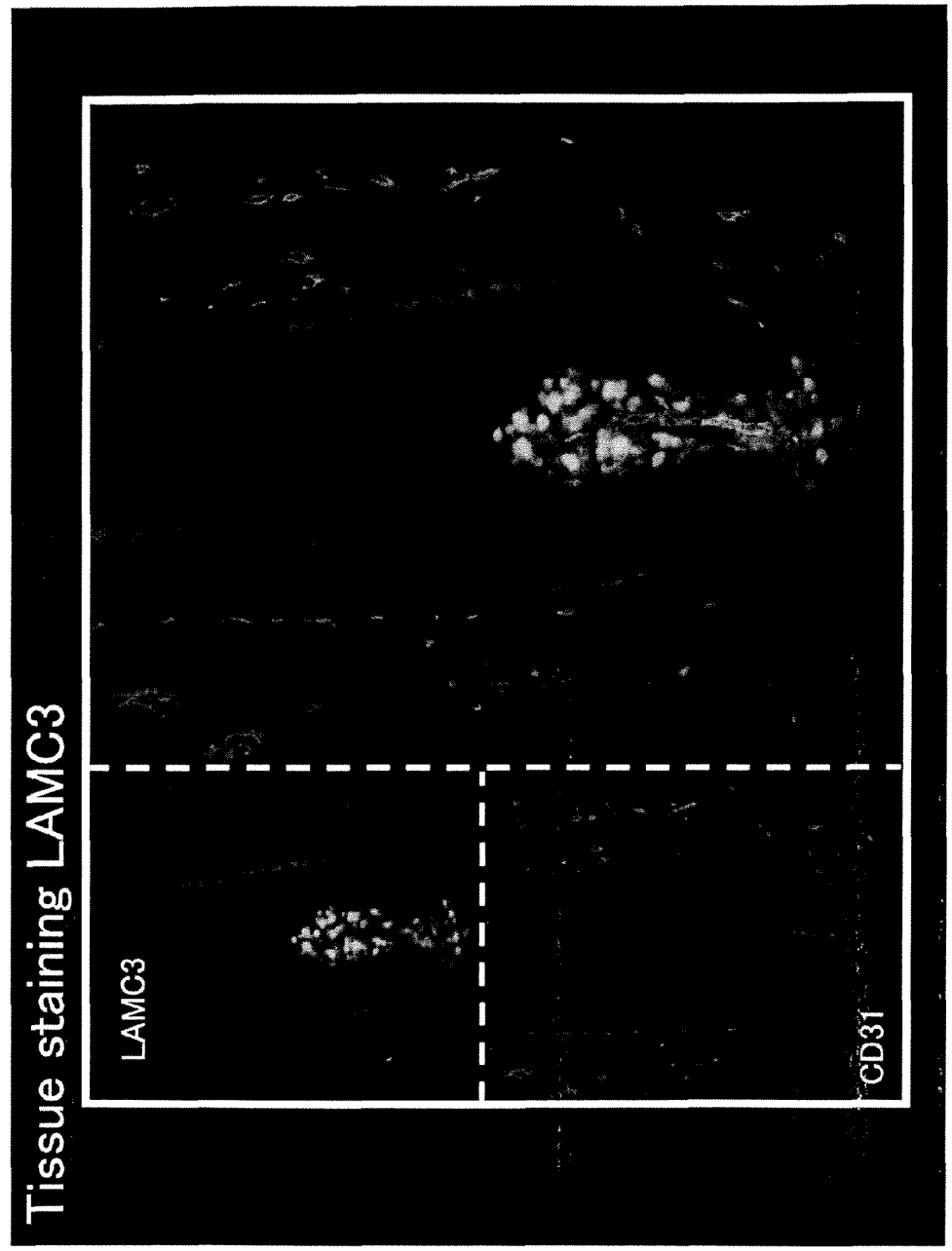
FIG. 2 is a photograph showing tissue staining of LAMC3 in dermal papilla cells.

A study of the localization in dermal papilla of the JAM2 and LAMC3 genes of the 21 genes belonging to GO:7155 (cell adhesion) that were highly expressed in DP cells for which expression levels were particularly high in DP cells and for which expression levels were low in DS cells based on microarray data. As a result, these genes were confirmed to be expressed in dermal papilla (FIGS. 1 and 2).

Figure 3:
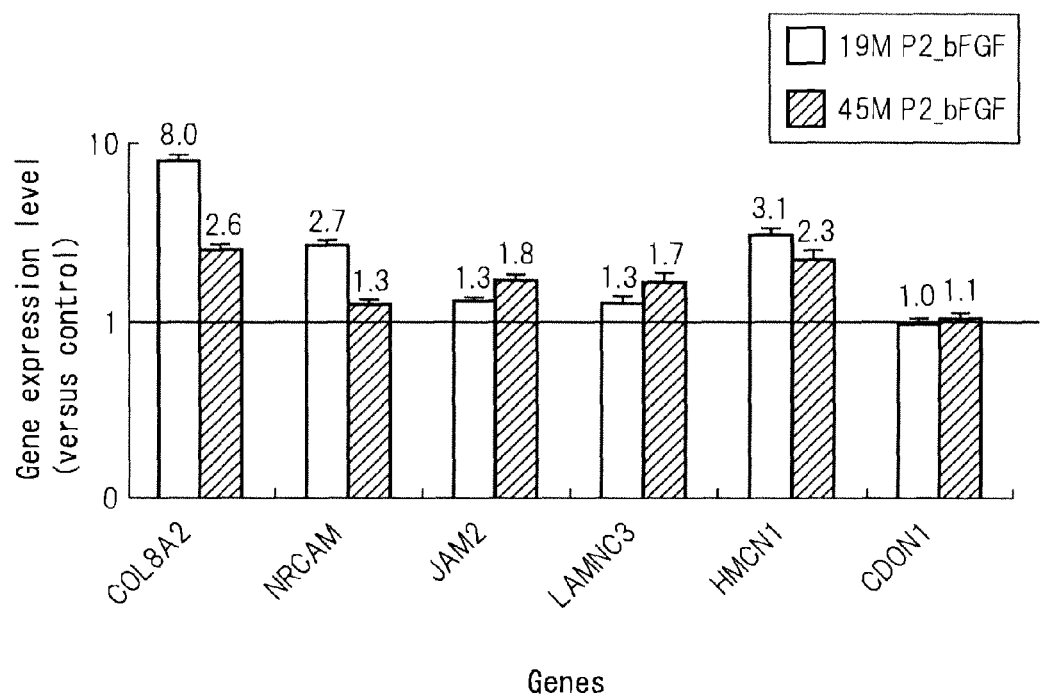
FIG. 3 is a graph showing increased expression of genes involved in cell adhesion in dermal papilla cells cultured in media to which was added bFGF in a comparison with a control (bFGF not added).

In the case of using cDNA obtained from DP cells cultured in the presence of bFGF as a template, all six type of genes shown in Table 2 demonstrated high levels of gene expression in two types of human DP cells of different origins (FIG. 3).

TABLE 2

| | | COL8A2 | NRCAM | JAM2 | LAMNC3 | HMCN1 | CDON1 |
|---|---|---|---|---|---|---|---|
| Mean | 19M P2 bFGF | 8.04 | 2.73 | 1.33 | 1.31 | 3.10 | 0.98 |
| | 45M P2 bFGF | 2.57 | 1.28 | 1.77 | 1.72 | 2.28 | 1.06 |
| SD | 19M P2 bFGF | 0.52 | 0.18 | 0.08 | 0.12 | 0.30 | 0.09 |
| | 45M P2 bFGF | 0.21 | 0.09 | 0.12 | 0.21 | 0.27 | 0.08 |

Since the expression levels of genes involved in cell adhesion that were found to be strongly expressed in DP cells was increased by bFGF, which is known to have an action that maintains the ability to induce hair follicles, formation and/or regeneration of hair follicles can be promoted by maintaining or increasing expression of these genes involved in cell adhesion in dermal papilla cells, and substances demonstrating the effect of maintaining activity of dermal papilla cells can be screened by using these genes as indicators.

[Sequence Listing]

The invention claimed is:

1. A method for culturing dermal papilla cells that maintain the ability to induce hair follicles, comprising: maintaining or increasing expression of one or a plurality of genes involved in cell adhesion belonging to GO:7155 in the dermal papilla cells, and sub-culturing those dermal papilla cells in which expression of the gene involved in cell adhesion has been maintained or increased; wherein the gene involved in cell adhesion is selected from the group consisting of HAPLN1 (SEQ ID NO:13), COL8A2 (SEQ ID NO:14), NRCAM (SEQ ID NO: 15), EDIL3 (SEQ ID NO:17), CX3CL1 (SEQ ID NO:18), CDON (SEQ ID NO:19), HMCN1 (SEQ ID NO:20), FRAS1 (SEQ ID NO:22), CDH4 (SEQ ID NO:23), MYBPH (SEQ ID NO:24), CDHR3 (SEQ ID NO:25), SLIT2 (SEQ ID NO:27), FN1 (SEQ ID NO:28), ITGBL1 (SEQ ID NO:30), PVRL3 (SEQ ID NO:31) and NRP2 (SEQ ID NO:26).

2. The method for culturing dermal papilla cells according to claim 1, wherein the gene involved in cell adhesion is selected from the group consisting of COL8A2 (SEQ ID NO:14), NRCAM (SEQ ID NO:15), HMCN1 (SEQ ID NO:20) and CDON (SEQ ID NO:19).

* * * * *

```
                           SEQUENCE LISTING

<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: forward primer

<400> SEQUENCE: 1
tgtacaagaa caacgtgccg                                                   20

<210> SEQ ID NO 2
<211> LENGTH: 20
<212> TYPE: DNA
<213> ORGANISM: Artificial
<220> FEATURE:
<223> OTHER INFORMATION: reverse primer

<400> SEQUENCE: 2
cgcctctgtt cagcttttgt                                                   20

<210> SEQ ID NO 3
<211> LENGTH: 20
<212> TYPE: DNA
<213> ORGANISM: Artificial
<220> FEATURE:
<223> OTHER INFORMATION: forward primer

<400> SEQUENCE: 3
tgatgcagaa gaccacaagc                                                   20

<210> SEQ ID NO 4
<211> LENGTH: 20
<212> TYPE: DNA
<213> ORGANISM: Artificial
<220> FEATURE:
<223> OTHER INFORMATION: reverse primer

<400> SEQUENCE: 4
agggctgaca aacaagtgct                                                   20

<210> SEQ ID NO 5
<211> LENGTH: 20
<212> TYPE: DNA
<213> ORGANISM: Artificial
<220> FEATURE:
<223> OTHER INFORMATION: forward primer

<400> SEQUENCE: 5
gccttgaggg atgaaaacct                                                   20

<210> SEQ ID NO 6
<211> LENGTH: 20
<212> TYPE: DNA
<213> ORGANISM: Artificial
<220> FEATURE:
<223> OTHER INFORMATION: reverse primer
```

-continued

```
<400> SEQUENCE: 6
ccaaggaagg cacacaaaac                                              20

<210> SEQ ID NO 7
<211> LENGTH: 20
<212> TYPE: DNA
<213> ORGANISM: Artificial
<220> FEATURE:
<223> OTHER INFORMATION: forward primer

<400> SEQUENCE: 7
agagcgtcaa ggacaatgtg                                              20

<210> SEQ ID NO 8
<211> LENGTH: 20
<212> TYPE: DNA
<213> ORGANISM: Artificial
<220> FEATURE:
<223> OTHER INFORMATION: reverse primer

<400> SEQUENCE: 8
gttaccggct tgaagttgga                                              20

<210> SEQ ID NO 9
<211> LENGTH: 20
<212> TYPE: DNA
<213> ORGANISM: Artificial
<220> FEATURE:
<223> OTHER INFORMATION: forward primer

<400> SEQUENCE: 9
aaagaaggga atccagctcc                                              20

<210> SEQ ID NO 10
<211> LENGTH: 20
<212> TYPE: DNA
<213> ORGANISM: Artificial
<220> FEATURE:
<223> OTHER INFORMATION: reverse primer

<400> SEQUENCE: 10
tagcatacac caaggccaca                                              20

<210> SEQ ID NO 11
<211> LENGTH: 20
<212> TYPE: DNA
<213> ORGANISM: Artificial
<220> FEATURE:
<223> OTHER INFORMATION: forward primer

<400> SEQUENCE: 11
tacgcgcttc tctggaatct                                              20

<210> SEQ ID NO 12
<211> LENGTH: 20
<212> TYPE: DNA
<213> ORGANISM: Artificial
<220> FEATURE:
<223> OTHER INFORMATION: reverse primer

<400> SEQUENCE: 12
ctgccatgat gcaactgtct                                              20
```